United States Patent
Moldes Menduina et al.

(10) Patent No.: US 12,383,847 B2
(45) Date of Patent: Aug. 12, 2025

(54) PROCESS FOR THE AQUEOUS EXTRACTION OF BIOSURFACTANTS FROM CORN STEEP LIQUOR

(71) Applicant: UNIVERSIDADE DE VIGO, Vigo (ES)

(72) Inventors: Ana Belen Moldes Menduina, Vigo (ES); Jose Manuel Cruz Freire, Vigo (ES); Lorena Rodriguez Lopez, Vigo (ES); Alejandro Lopez Prieto, Vigo (ES)

(73) Assignee: UNIVERSIDADE DE VIGO, Vigo (ES)

( * ) Notice: Subject to any disclaimer, the term of this patent is extended or adjusted under 35 U.S.C. 154(b) by 773 days.

(21) Appl. No.: 17/605,812

(22) PCT Filed: May 19, 2020

(86) PCT No.: PCT/ES2020/070321
§ 371 (c)(1),
(2) Date: Oct. 22, 2021

(87) PCT Pub. No.: WO2020/234501
PCT Pub. Date: Nov. 26, 2020

(65) Prior Publication Data
US 2022/0203262 A1 Jun. 30, 2022

(30) Foreign Application Priority Data
May 21, 2019 (ES) .................. 201900084

(51) Int. Cl.
*B01D 11/02* (2006.01)
*A23L 33/10* (2016.01)
*B01D 21/26* (2006.01)
*C09K 23/24* (2022.01)
*C11D 9/02* (2006.01)

(52) U.S. Cl.
CPC .......... *B01D 11/0288* (2013.01); *A23L 33/10* (2016.08); *B01D 21/26* (2013.01); *C09K 23/24* (2022.01); *C11D 9/02* (2013.01); *A23V 2002/00* (2013.01)

(58) Field of Classification Search
CPC ..... B01D 11/0288; B01D 21/26; A23L 33/10; C09K 23/24; C11D 9/02
See application file for complete search history.

(56) References Cited

FOREIGN PATENT DOCUMENTS

| EP | 2862624 A1 | 4/2015 | |
|---|---|---|---|
| ES | 2424399 A1 | 10/2013 | |
| ES | 2527366 B1 | 11/2015 | |
| WO | WO-9632122 A1 * | 10/1996 | ......... A61K 31/4184 |
| WO | 2014044876 A1 | 3/2014 | |

OTHER PUBLICATIONS

Vecino et al, "Optimization of extraction conditions and fatty acid characterization of Lactobacillus pentosus cell-bound biosurfactant/bioemulsifier", J Sci Food Agric 2015; 95: 313-320 (Year: 2015).*
Vecino, Optimization of extraction conditions and fatty acid characterization of Lactobacillus pentosus cell-bound biosurfactant/emulsifier,, J Sci Food Agric, 2015; 95: 313-320 (Year: 2015).*
Hofer, Process Biochemistry, 70, 2018, 20-28 (Year: 2018).*
P. Jamal, et al., "Production of Biosurfactant in 2L Bioreactor Using Sludge Palm Oil as a Substrate", Iium Engineering Journal, vol. 12, No. 4, pp. 109-113, 2011.
X. Vecino, et al., "Optimization of Liquid-Liquid Extraction of Biosurfactants From Corn Steep Liquor", Bioprocess Biosyst Eng, 28 pages, 2015.
International Search Report for Corresponding International Application No. PCT/ES2020/070321, Jul. 28, 2020 and English Translation.

* cited by examiner

*Primary Examiner* — Andrew D Kosar
*Assistant Examiner* — Phillip Matthew Rzeczycki
(74) *Attorney, Agent, or Firm* — LUCAS & MERCANTI, LLP

(57) ABSTRACT

A process for extracting biosurfactants from the solid content in corn steep liquor, using a buffered aqueous solution having a pH of 6-8 and a biosurfactant extract obtained using the process of the invention, and the uses in cosmetics, food, pharmaceutical, agrochemical and environmental industries. The obtained biosurfactant has the form of a white powder with foaming capacity and is able to reduce water surface tension by at least 16-20 units.

20 Claims, 3 Drawing Sheets

PROCESS FOR THE AQUEOUS EXTRACTION OF BIOSURFACTANTS FROM CORN STEEP LIQUOR

CROSS REFERENCE TO RELATED APPLICATION

This application is a 371 of PCT/ES2020/070321, filed May 19, 2020, which claims the benefit of Spanish Patent Application No. P201900084 filed May 21, 2019, each of which are incorporated herein by reference.

FIELD OF THE INVENTION

The present invention belongs to the field of obtaining detergents of natural origin, called biosurfactants.

The main purpose of the invention is to obtain a biosurfactant extract obtained from corn steep liquor (CSL), generated during the wet fractionation of corn, using a buffered aqueous saline solution or a buffer solution as the sole extracting agent.

BACKGROUND

Corn steep liquors (CSL) are a residue of the wet corn fractionation industry (Singh and Eckhoff, 1996, Yan et al 2005, Ramirez et al 2008). These liquors are composed of water and solids (Ramirez et al 2008). The concentration of solids in these liquors can reach up to 50% by weight, when they are subjected to a process of water evaporation. In fact, most corn steep liquors that are marketed as a low-cost nutritional supplement, in biotechnological processes or for animal feed, contain around 50% solids (See the percentage in solids of Corn Steep Liquors marketed by Sigma Aldrich, Santa Cruz Biotechnology, or FeedStimulants). The solid fraction of these liquors is formed mainly by microbial biomass that dies during the maceration process, as well as by substances that have not reached the necessary degree of solubility from corn. It is known that, during the maceration process of corn, lactic bacteria, among other microorganisms, grow for its wet fractionation (Yang et al 2005), which is why corn steep liquors contain a high concentration of lactic acid.

On the other hand, in recent years the existence of biosurfactants in corn steep liquor (CSL) has been demonstrated in various publications and patents (Vecino et al 2014, Vecino et al 2015, Rodriguez-López et al 2017, Patent WO2014/044876 A, Patent ES 2 424 399, Patent ES 2 527 366 B1), from the spontaneous fermentation of these liquors by microorganisms that grow during the maceration process of corn. So far, the only process described for obtaining these biosurfactants from CSL consists of a liquid-liquid extraction, mainly using organic solvents such as chloroform or ethyl acetate (Patent WO2014/044876). Vecino et al 2015 also collects the use of other solvents such as Isoamyl alcohol; Tributyl Phosphate (TBP); Methyl butyl ether (MTBE); Trichlorethylene (TCE); Dichloromethane; Xylene; Hexane or Heptane, in addition to chloroform and ethyl acetate. FIG. 1 shows a flow diagram of the process followed so far to obtain biosurfactants from corn steep liquors.

It should be emphasized that the use of organic solvents can be a disadvantage when applying this biosurfactant extract in certain industrial sectors, mainly in the pharmaceutical sector, so it would be interesting to use alternative methods that allow to obtain biosurfactants from these liquors, using extractants that are more biocompatible and have less environmental impact.

Below are some bibliographically proven uses of biosurfactants obtained from corn steep liquors by liquid-liquid extraction with organic solvents: i) on a soil and sludge treatment level, it has been observed that the use of this biosurfactant extract favors the solubilization and subsequent biodegradation of polycyclic aromatic hydrocarbons (Vecino et al 2014, Vecino et al 2015); ii) On a cosmetic level, tests have been carried out with this biosurfactant extract on human hair (Rincón-Fontán et al 2016, Rincón Fontán et al 2017), observing an improvement in the physical characteristics of the hair covering after the treatment with the biosurfactant extract obtained from (CSL), compared to the chemical surfactant sodium dodecyl sulfate (SDS); iii) the use of the biosurfactant extract in the formulation of gold and silver nanoparticles has also been evaluated (Gómez-Graña et al 2017), observing that this extract not only has surfactant capacity, replacing the cationic surfactant Cetyltrimethylammonium bromide (CTAB), it also has a reducing capacity that avoids the use of synthetic reducing agents in the formulation of these nano emulsions. Gold particles are introduced in many cosmetic formulations in order to promote the nutrition, luminosity, and vitality of the skin. In addition, Rodriguez-López et al 2019 has also corroborated the improvement of the permeation of active principles through the skin, in the presence of the biosurfactant extract obtained from corn steep liquors, through extraction with organic solvents. On the other hand, López-Prieto et al 2019 has applied this same biosurfactant extract in the formulation of drinkable yogurts in order to improve their rheological properties, the probiotic biomass contained in the yogurt not being affected.

As already mentioned above, corn steep liquors have a high solids content, generally 50% w/w. A high percentage of these solids is represented by the microbial biomass that grows during the maceration process of corn (Ramirez et al 2008). Within the microbial flora present in corn steep liquors, there are, among others, lactic acid bacteria. Various works have demonstrated the presence of biosurfactants adhered to the plasma membrane of this type of bacteria (Velraeds et al 1996, Rodriguez-López et al 2018, Vecino et al 2018), although so far, the extraction of biosurfactants from the solid fraction of corn steep liquors, by means of solid-liquid extraction, has not been contemplated.

On the other hand, it should be noted that there is no evidence to date of obtaining biosurfactants from corn steep liquors by using an aqueous solution as an extractant.

As mentioned before, biosurfactants can be applied in different industrial fields and each biosurfactant extract can be considered unique, because each microorganism produces biosurfactants in a very specific way. Thus, small changes in the composition of the fermentation medium or in the operating variables cause the microorganisms to produce different biosurfactants at a compositional level, varying in many cases the length of the fatty acids or the amino acids that constitute them (Mata-Sandoval et al. al 2001, Singh et al 2014, Vecino et al 2017). In fact, it has been shown that, even under the same operating conditions, the same microorganism can produce different biosurfactants, depending on the growth phase in which it is found (Velraeds et al 1996, Angelo et al 2003).

Currently, regarding the uses of biosurfactants, the industry that can best deal with their inclusion in formulations is the cosmetic industry, given the high added value of its products. This is because the biotechnological production of biosurfactants, through controlled fermentations, requires large investments. Table 1 lists the biosurfactants included so far in the European list of cosmetic Ingredients (CosIng).

TABLE 1

List of biosurfactants included in the Cosing and their functions

| Biosurfactant | Microorganism | Function |
| --- | --- | --- |
| Rhamnolipids | *Pseudomonas aeruginosa* | Emollient Emulsifier |
| Soforolipids obtained by using palm hydrolysates as substrates | Candida bombicola | Conditioner Protector Detergent Antioxidant Antiseborrheic |
| Soforolipids | *Starmerella bombicola* | Cleaner Emulsifier Surfactant Antimicrobial |
| Soforolipids obtained by using rapeseed as substrate | Candida bombicola | Cleaner Deodorant Surfactant Cleaner |
| Sodium Surfactin | *Bacillus subtillis* | Emulsifier Gelling Surfactant |

BRIEF DESCRIPTION OF THE DRAWINGS

To complement the description made and in order to reach a better understanding of the features of the invention, a set of drawings is attached as an integral part of said description, in which, with an illustrative and non-limiting nature, the following has been represented.

DETAILED DESCRIPTION OF THE INVENTION

Figure 1:
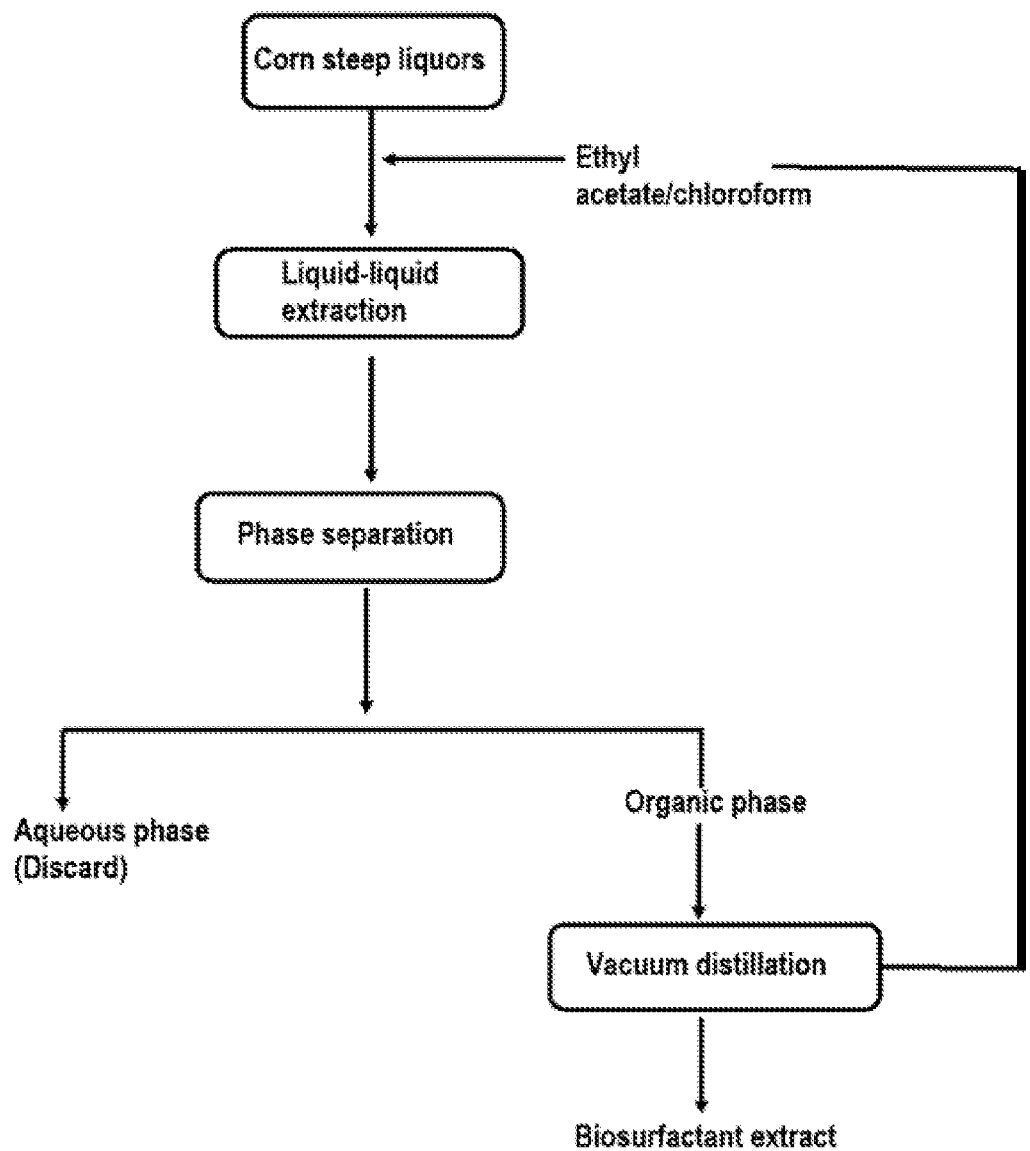
FIG. 1. Scheme of the process proposed so far to obtain biosurfactants from corn steep liquors. In this scheme, corn steep liquors, which can contain a percentage of solids between 18 and 50%, are subjected to a liquid-liquid extraction process with organic solvents such as ethyl acetate or chloroform, for 1-2 h, depending on the selected solvent. During this process, the biosurfactants contained in the corn steep liquors pass to the organic phase, which is subsequently separated from the aqueous phase of the liquors and is subjected to a vacuum distillation process, thus obtaining a biosurfactant extract. The biosurfactant extract obtained has an oily appearance and has no foaming capacity.
Figure 2:
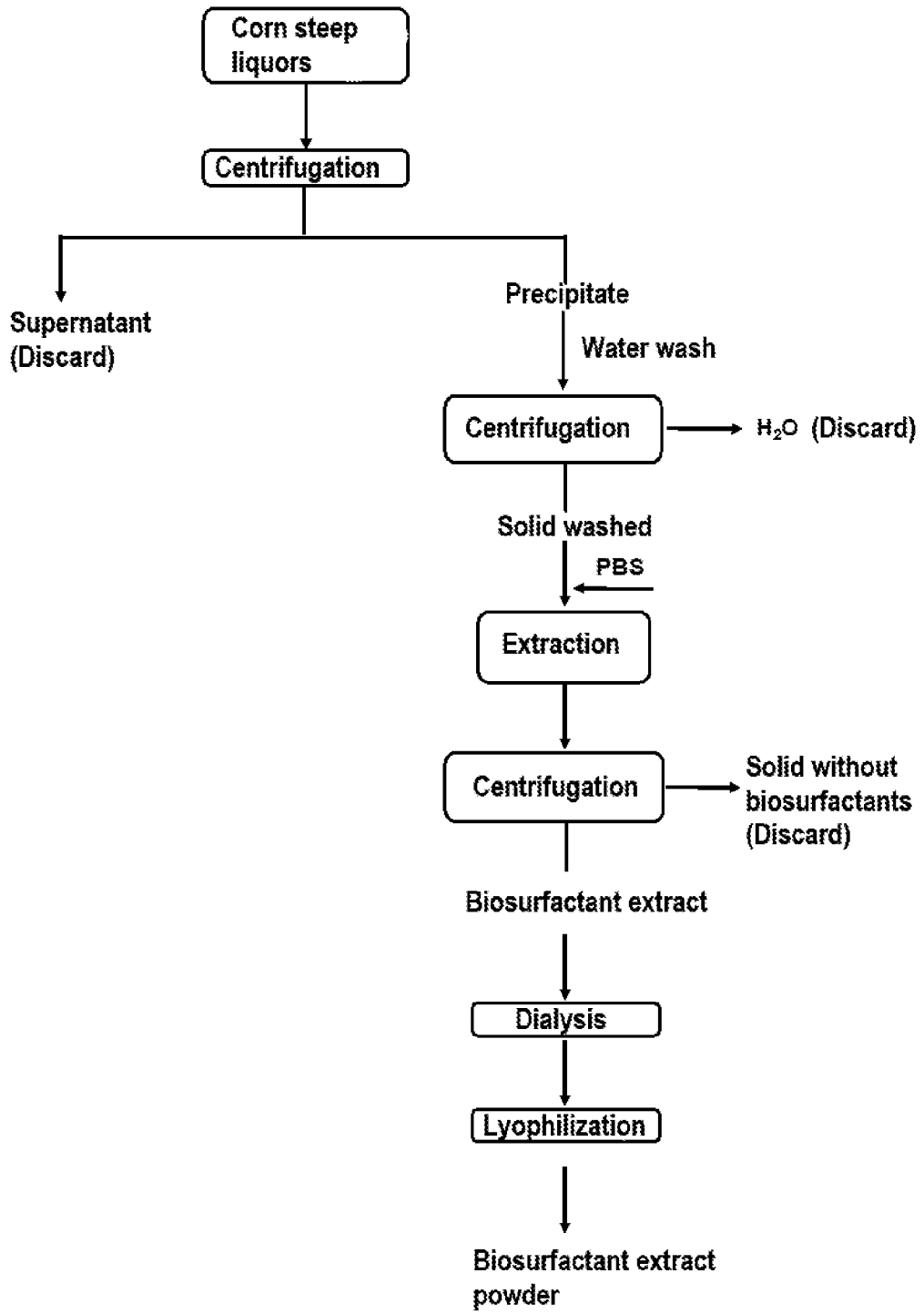
FIG. 2. Scheme proposed in this invention to obtain biosurfactants from corn steep liquors. In this scheme, we start from corn steep liquors with 50% solids, which are centrifuged, thus obtaining a precipitate that is washed several times with water, discarding the supernatant. Subsequently, the precipitate is subjected to an extraction process with phosphate buffered saline (PBS) or simply with phosphate buffer. After the extraction process, an aqueous phase with biosurfactants is obtained, which is recovered by centrifugation and subjected to a dialysis process. In this way the present salts are eliminated. Finally, the resulting solution is lyophilized, obtaining a white powder with biosurfactant capacity, capable of forming foam in aqueous solution.

The present invention refers to a process for obtaining biosurfactants from corn steep liquors (CSL), comprising the steps of:

separation of the solid phase from the CSL, and
contacting the separated solid phase with a buffered aqueous solution which has a pH of 6 to 8.

The process of the present invention is a solid-liquid extraction process, by which the buffered aqueous solution extracts the biosurfactants present in the solids of the CSL. Therefore, it is necessary to separate the solid phase from the liquid phase that constitute corn liquors. Within the scope of the present invention, "CSL solid phase" and "CSL solids" are synonymous with and interchangeable with each other.

Any solid-liquid separation process known in the art, such as centrifugation or filtration, can be used to separate the solid phase from the CSLs. Preferably, the CSL solids separated in this way are washed with water to remove impurities present in the solids and improve the extraction performance of the biosurfactants. Said washes are preferably carried out with deionized water. Furthermore, such washes preferably occur at room temperature (typically 10 to 25° C.).

To extract the biosurfactants, the solid phase of the CSL, once separated and preferably washed, is put in contact with a buffered aqueous solution with a pH of 6 to 8.

Therefore, the buffered aqueous solution uses a buffering agent to maintain a pH in the solution of 6 to 8, preferably around 7.0, such as between 6.5 and 7.5. The pH of the buffered aqueous solution should be such that it minimizes or prevents cell lysis and the consequent release of cell contents, since this can hinder the extraction and purification of the biosurfactants. Examples of buffering agents that can be used in accordance with the invention include phosphate salts, carbonate salts, and combinations of these. Preferably, the buffering agent is a phosphate salt, such as $KH_2PO_4$, $K_2HPO_4$, and/or $Na_2HPO_4$.

The buffered aqueous solution may comprise at least one salt selected from the group that consists of sodium chloride, potassium chloride, calcium chloride, and magnesium chloride, and combinations thereof.

Preferably, the buffered aqueous solution is isotonic. Within the scope of the present invention, "isotonic" is a solution whose osmotic concentration varies between 280 and 315 mOsm/L. Said osmotic concentration can be achieved, for example, by adjusting the concentration of at least one salt selected from the group that consists of sodium chloride, potassium chloride, calcium chloride and magnesium chloride, and combinations of these. Isotonicity prevents cell lysis of microorganisms present in the solid phase of CSL, and the consequent release of cell content, which can hinder the extraction and purification of biosurfactants.

However, it has been found that the buffered aqueous solution of the invention is capable of extracting biosurfactants with the same characteristics with osmolarities lower than 280 mOsm/L, as low as 20 and 30 mOsm/L. The inventors believe that this is possible because the biosurfactants present in the solid fraction of the CSL are bound externally to the cell membrane of the microorganisms present in the CSL and during the extraction processes the osmotic pressure is balanced on both sides of the plasma membrane of the microorganisms present in corn steep liquors, through the release of the biosurfactants present in their plasma membrane.

Therefore, it is possible to perform the extraction with a buffered aqueous solution with an osmolarity of at least 20 mOsm/L, such as at least 30 mOsm/L, at least 50 mOsm/L, at least 100 mOsm/L, at least 150 mOsm/L, at least 200 mOsm/L, and at least 250 m/Osm/L. Osmolarities less than 280 mOsm/L can be achieved, for example, with low concentrations of the at least one salt selected from the group that consists of sodium chloride, potassium chloride, calcium chloride, and magnesium chloride, and combinations of these.

In a preferred aspect, the buffered aqueous solution is phosphate buffered saline (PBS). The PBS solution is isotonic and has a pH between 7.3 and 7.5. It is composed of at least one phosphate salt, such as $KH_2PO_4$, $K_2HPO_4$, and/or $Na_2HPO_4$ as a buffer, and at least one salt selected from the group that consists of sodium chloride, potassium chloride, calcium chloride, and magnesium chloride.

The contacting of the separated solid phase with the buffered aqueous solution can be carried out for a time of at least 20 minutes, preferably at least 1 hour, for example, at least 1.5 hours. Although the contact time can be extended beyond 2.0 hours, a time of between 20 minutes and 2.0 hours is preferred. Furthermore, contacting can occur at a temperature of 10° C. to 70° C. The extraction time varies depending on the temperature: the lower the temperature, the longer the extraction time. For the economy of the process, the extraction is preferably carried out at room temperature (10-25° C.), without the use of heating or cooling equipment.

The extraction time can also vary depending on the presence or absence of the at least one salt selected from the group that consists of sodium chloride, potassium chloride, calcium chloride, magnesium chloride and combinations of these, in the buffered aqueous solution. For example, extraction at room temperature will take longer in the absence of NaCl and/or KCl.

The contacting of the separated CSL solid phase with the buffered aqueous solution can be carried out in a discontinuous or semi-continuous process, in an equipment suitable for solid-liquid separation. For example, one or more reactors can be used with stirring, depending on the operating regime, discontinuous (one could be sufficient) or semi-continuous (several reactors would be coupled in series). Preferably, the CSL solids are washed in the reactors, as well as the biosurfactant extraction process, both processes being independent but sequential.

Generally, after the contacting step, the buffered aqueous solution, which also contains the biosurfactants, is separated from the CSL solids, so that an extract of biosurfactants is obtained. Said separation can be carried out with any solid-liquid separation process known in the art, such as centrifugation or filtration.

Therefore, it is possible to couple a membrane filtration system or a centrifugation process after the washing and/or extraction process, to recover the solids after the washing, or to remove them after the extraction process. The biosurfactant extract thus obtained can also be dialyzed to remove salts, concentrated and/or processed for long-term storage.

By means of the process of the invention, it is possible to extract a biosurfactant from corn steep liquors other than those obtained with the processes described in the art.

After the analysis of the biosurfactant extract, using electrospray mass spectrometry, it is observed that the biosurfactant extract obtained by this route presents differentiating biomarkers from the other biosurfactants collected in the bibliography, and also presents a different aspect and surfactant capacity to the biosurfactant extract obtained from corn steep liquors by extraction with organic solvents, therefore it can be deduced that corn steep liquors contain different types of biosurfactants, probably produced by different classes of microorganisms.

Consequently, the present invention also relates to a biosurfactant obtained or obtainable by means of the process for obtaining biosurfactants, as described.

Said biosurfactant extract is useful as a surfactant, emulsifier and/or emulsifier agent in the food, cosmetic, pharmaceutical, agrochemical or environmental industries. Examples of application of the biosurfactant extract include the emulsion and/or stabilization of active principles in aqueous and/or oily solutions; surface cleaning; and to improve the permeability of those formulas that contain active ingredients through cell membranes.

EMBODIMENTS

Example 1. Formulations of the Isotonic Buffered Aqueous Solution

This example illustrates formulations of buffered solutions, with varying concentrations of salt, which can be used to extract the biosurfactants present in the microbial biomass of CSL.

Formulation 1 (PBS):
  10 mM $KH_2PO_4/K_2HPO_4$
  150 mM NaCl
Formulation 2 (PBS):
  137-150 mM NaCl
  2.7 mM KCl
  10 mM $Na_2HPO_4$
  1.8 mM $KH_2PO_4$
Formulation 3 (Krebs-Henseleit Buffer) Glucose-Free:
  Magnesium sulfate 0.141 g/L
  Monobasic potassium phosphate 0.16 g/L
  Potassium chloride 0.35 g/L
  Sodium chloride 6.9 g/L
Formulation 4:
  Sodium Chloride 120 mM
  Potassium Chloride 5 mM
  Calcium Chloride Dihydrate 2 mM
  Magnesium Chloride Hexahydrate 1 mM
  Sodium Bicarbonate 25 mM
Formulation 5 (Carbonate Buffer):
  Sodium bicarbonate 0.0125 M
  Sodium carbonate 0.0875 M Example 2. Obtaining the Biosurfactant Extract Extractions were made to corn steep liquors from the wet corn fractionation process, supplied by FeedStimulants (Utrecht, The Netherlands).

The corn steep liquors were taken and subjected to a centrifugation process, in order to obtain the solid fraction contained in these liquors, which, once the supernatant had been eliminated, was washed several times with deionized water at room temperature, repeating the spin process, between each wash cycle.

Subsequently, the solids, from the corn steep liquors, once washed and centrifuged, were subjected to an extraction process with Formulation 1 of Example 1 (with the pH adjusted to 7.4). The extraction process was carried out for 2 hrs, at room temperature. After the extraction, the saline solution and the solid fraction of the corn washing liquors were centrifuged, obtaining a biosurfactant extract and a solid precipitate, which was discarded.

In addition, extractions were carried out with Formulation 1 of Example 1, only removing the NaCl (buffered aqueous solution). In this case, to obtain comparable yields, it was necessary to work at temperatures above 50° C., particularly between 50° C. and 65° C., following the same washing and centrifuging protocol as previously described.

Additionally, when using a buffered aqueous solution with reduced salt concentrations, it was observed that operating times, between 20 minutes and 2 hours, and extraction temperatures, between 10° C. and 70° C., also produce a biosurfactant extract with similar characteristics, although with different yields and productivity.

Table 2 provides an example of some of the conditions used during the extraction process.

TABLE 2

Selected conditions for obtaining the biosurfactant extract from corn steep liquors.

| Solvent | Extraction Agent | Time | Temperature (° C.) |
|---|---|---|---|
| Conditions selected as optimal for obtaining biosurfactants | | | |
| Water | Physiological phosphate-buffered saline, (PBS) | 2 hrs | Environment |
| Water | Phosphate buffer, (0% NaCl, 0% KCl) | 1.5 hrs | 65° C. |
| Other formulations with the ability to extract biosurfactants | | | |
| Water | NaCl; KCl; $Na_2HPO_4$ | 20 min-2 hrs | 10-70° C. |
| Water | NaCl; $KH_2PO_4/K_2HPO_4$ | 20 min-2 hrs | 10-70° C. |
| Water | $H_2CO_3/NaHCO_3$ | 20 min-2 hrs | 10-70° C. |
| Water | $H_2CO_3/KHCO_3$ | 20 min-2 hrs | 10-70° C. |
| Water | $Na_2HPO_4$ | 20 min-2 hrs | 10-70° C. |
| Water | $KH_2PO_4/K_2HPO_4$ | 20 min-2 hrs | 10-70° C. |

Example 3. Analysis of the Extract

Once the biosurfactant extract was obtained, it was dialyzed and lyophilized, to be subsequently subjected to various analyzes, including elemental analysis, surfactant capacity (based on measurement of surface tension), calculation of the critical micellar concentration, evaluation of the foaming capacity and mass analysis by electrospray-type mass spectrometry.

The analysis of the biosurfactant extract (dialyzed and lyophilized) revealed that it is capable of reducing at least the surface tension of the medium by 16-20 units and that it presents a maximum critical micellar concentration (CMC) of around 420 mg/L, although the CMC can vary depending on the degree of purity achieved during the extraction process.

Additionally, biosurfactant extracts were identified by using electrospray ionization/collision-induced dissociation mass spectrometry (ESI-MS/CID). For analysis, 1 mg of each sample was diluted in chloroform and volatilized by vacuum distillation. Next, a stream of electrons was used to ionize and fragment the molecules. Finally, the fragmentation patterns were recorded on a Bruker FTMS APEXIII mass spectrometer (Fremont, CA) in positive mode. On the other hand, an elemental analysis of the different extracts was carried out by chromatographic combustion using a Carlo Erba 1108 Elemental Analyzer.

Mass spectrometry analysis (FIG. 3) reveals that the biosurfactant produced is a lipopeptide, although it also has other substances with surfactant capacity, including glycopeptides and high molecular weight proteins, with molecular masses below 900 m/z.

Figure 3:
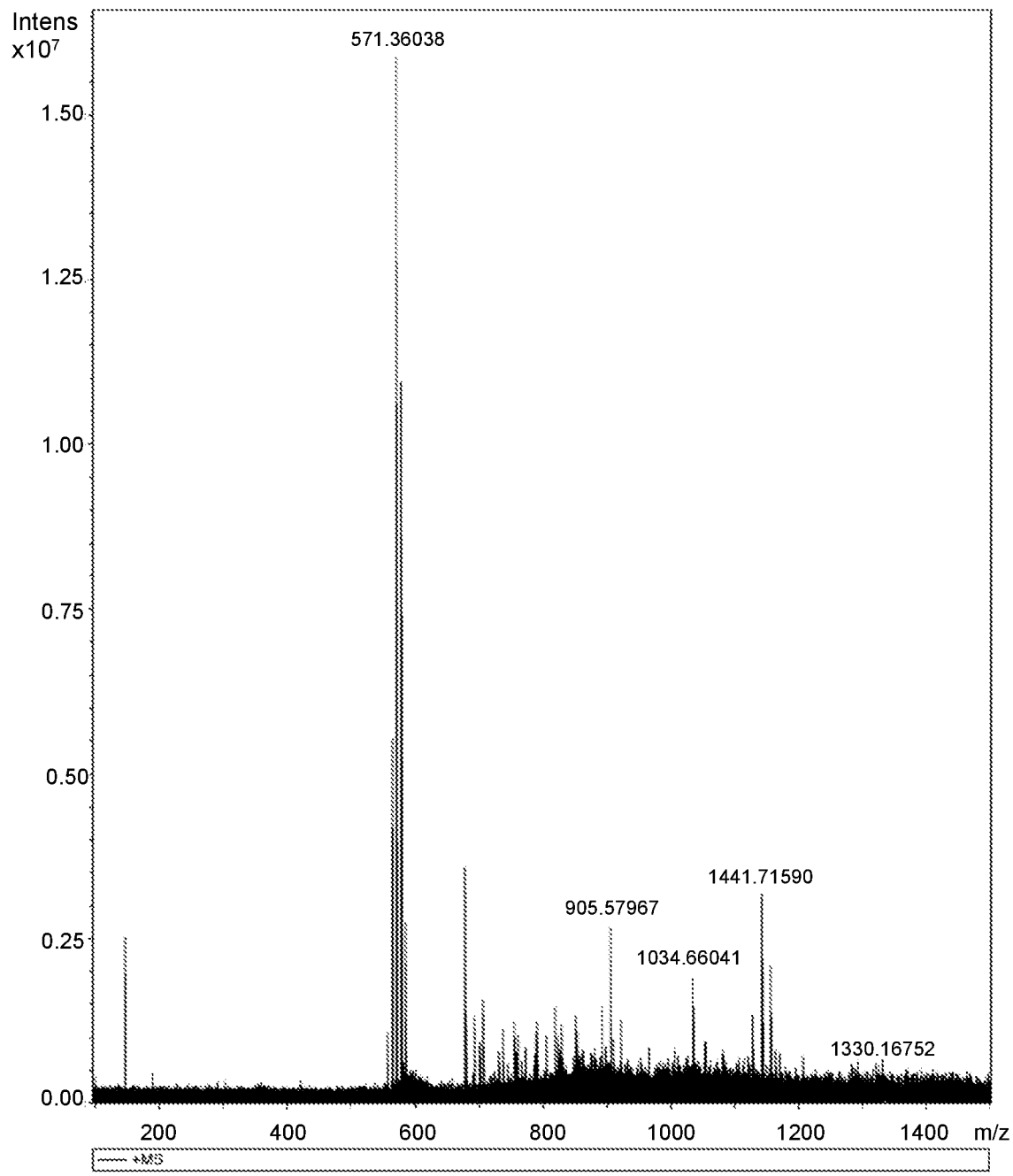
FIG. 3. Mass spectrum of the biosurfactant extract under study, in which a series of biomarkers between 905, 1034 and 1141 m/z are observed that correspond to the mass of the biosurfactant object of this invention and which fall within the range of masses of biosurfactants of a lipopeptide nature.

After the characterization, it is observed that the biosurfactant extract obtained has a different appearance and composition to the biosurfactant extracted from the corn steep liquors by extraction with organic solvents. Thus, the biosurfactant extract obtained by extraction with organic solvents has a yellow color, is viscous, has an oily appearance and does not have the ability to form foam. However, the biosurfactant extract, object of this invention, has the appearance of a white powder and has the ability to form foam. Regarding its elemental composition, the extract object of this invention, which corresponds to the mass spectrum of FIG. 3, is composed of an average composition of: 12.5% N, 42.5% C, 6.2% H and less 0.3% sulfur.

Table 3 shows by way of example the composition obtained after elemental analysis of different extracts obtained from several batches of corn steep liquors and using different extractant solutions comprising phosphate buffered saline or non-saline phosphate buffer.

TABLE 3

Elemental analysis of the extracts

| Batch | Extractant | N (%) | C (%) | H (%) |
|---|---|---|---|---|
| 1a | non-saline phosphate buffer | 6.14 | 30.15 | 4.42 |
| 1b | non-saline phosphate buffer | 7.81 | 29.59 | 4.5 |
| 2a | non-saline phosphate buffer | 7.36 | 39.79 | 6.02 |
| 2b | non-saline phosphate buffer | 7.42 | 39.81 | 6.03 |
| 3a | PBS | 12.64 | 37.37 | 5.51 |
| 3b | PBS | 12.49 | 37.21 | 5.70 |
| 4a | PBS | 8.22 | 42.02 | 6.17 |
| 4b | PBS | 8.42 | 41.67 | 6.30 | a and b refer to different samples of biosurfactant from the same batch.

Both the composition, the appearance, and the physicochemical properties of the biosurfactant extract, object of this invention, are different from the biosurfactant extract extracted from the previously used corn steep liquors (Patent WO2014/044876 A, Patent ES 2 424 399, Patent ES 2 527 366 B1). Probably the difference in the appearance and composition of this new biosurfactant extract is due to the fact that in the previous inventions the biosurfactant extract is obtained from the liquid fraction, where the biosurfactants present in it are produced extracellularly, by the microorganisms that grow spontaneously there, while the biosurfactant under study is probably adhered to the plasma membrane of the microorganisms present in corn steep liquors, changing its nature. There are even strains of microorganisms that produce extracellular biosurfactants when they are in a vegetative state and non-extracellular biosurfactants when they grow in a sporulated way, and their characteristics and properties may vary (Angelo et al 2003). On the other hand, the biosurfactant extract obtained by extraction with organic solvents from corn steep liquors, has other substances in its composition (such as free fatty acids or antioxidants) that give the whole extract different characteristics (Rodriguez-López et al 2016), to the biosurfactant extract under study.

In the analysis of the biosurfactant extract, object of this invention, through mass spectrophotometry, by electrospray, several biomarkers are observed at 905, 1034 and 1141 m/z (FIG. 3) that may correspond to biosurfactant masses of a lipopeptide nature. It should be noted that microorganisms in general produce very specific biosurfactants depending on the fermentation medium where they grow, being very difficult to find two identical biosurfactants obtained from different media. Even during the same fermentation process, microorganisms can produce different types of biosurfactants depending on the growth phase in which they are found (Velraeds et al 1996, Angelo et al 2003). In fact, FIG. 3 shows several signals above 900 m/z that are probably due to this fact.

Furthermore, it has been observed that the biosurfactant extract, object of this invention, can comprise other biomolecules with surfactant capacity that comprise other glycopeptides, as well as high molecular weight proteins that can undergo hydrolysis and/or glycosylation processes, resulting in mass spectrum to biomarkers between 400 and 900 m/z, among which the following biomarkers stand out: 706 m/z, 642 m/z; 486 m/z; 536 m/z, 571 m/z.

It should be noted that the biosurfactant, object of this invention, has biomarkers and masses different from those listed in the bibliography and that therefore have not yet been applied in any industrial field, including cosmetic, pharmaceutical, environmental, agrochemical, or food.

Thus, Chen et al (2017) has produced a lipopeptide using *Bacillus licheniformis* with biomarkers at 994, 1008, 1022 and 1036 m/z, while Bechet et al. (2012) also produced a lipopeptide with surfactant capacity using *Bacillus thuringiensis*, in which biomarkers were identified at 879, 893, 893, and 907 m/z. On the other hand, Madonna et al (2003) produced several homologues of the biosurfactant produced by *Bacillus subtilis* with biomarkers at 892, 906 and 920 m/z. Furthermore, Li et al (2016) found that *Bacillus pseudomycoides* produces a lipopeptide with surfactant capacity with a main signal at 933 m/z, and other lower signals at 1533, 1231 and 1024 m z, which correspond to different biosurfactants produced by the same strain at different stages of growth. Angelo et al (2003) observed that *Bacillus globigii* produces different biosurfactants depending on whether it is in a vegetative or a sporulated state.

It should be noted that the biosurfactants described above are lipopeptides that present biomarkers close to those of the biosurfactant object of this invention, although none coincides in its entirety with the biosurfactant extracted from the corn steep liquors by extraction with PBS and object of study. It should also be noted that these biosurfactants were produced in controlled fermentations with fermentation media other than corn steep liquors, unlike the biosurfactant object of this invention. Furthermore, the biosurfactants mentioned in these works have been extracted from the fermentation medium, using methods other than the extraction with aqueous solution proposed in this invention.

The invention claimed is:

1. A process for the extraction of biosurfactants from corn steep liquors (CSL) comprising:
    a) separating a solid phase from the CSL, and
    b) contacting the separated solid phase with a buffered aqueous solution that has a pH of 6 to 8 and an osmotic concentration of at least 20 mOsm/L.

2. The process according to claim 1, further comprising, prior to step b), washing the separated solid phase with water.

3. The process according to claim 1, wherein the pH of the buffered aqueous solution has a pH of between 6.5 and 7.5.

4. The process according to claim 1, wherein the buffered aqueous solution has an osmotic concentration of between 20 and 315 mOsm/L.

5. The process according to claim 1, wherein the buffered aqueous solution comprises a buffering agent selected from a phosphate salt, a carbonate salt, or combinations thereof.

6. The process according to claim 1, wherein the buffered aqueous solution comprises at least one salt selected from the group consisting of sodium chloride, potassium chloride, calcium chloride, magnesium chloride, and combinations thereof.

7. The process according to claim 1, wherein the buffered aqueous solution is a phosphate buffered saline solution (PBS).

8. The process according to claim 1, further comprising contacting the separated solid phase with the buffered aqueous solution for at least 20 min.

9. The process according to claim 1, further comprising contacting the separated solid phase with the buffered aqueous solution at a temperature of 10° C. to 70° C.

10. A biosurfactant obtained by the process of claim 1, wherein the biosurfactant has a maximum critical micelle concentration of 420 mg/L, and the elemental composition of the biosurfactant is: between 6.14 and 7.81% of N, between 29.59 and 39.81% of C, between 4.42 and 6.03% of H, wherein the buffered aqueous solution is a non-saline phosphate buffer.

11. A surfactant and/or emulsifying agent for use in the food, cosmetic, pharmaceutical, agrochemical or environmental industry comprising the biosurfactant of claim 10.

12. A surfactant, emulsifier and/or stabilizer for use in cosmetic, pharmaceutical, and agrochemical purposes comprising the biosurfactant of claim 10.

13. A surface cleaner comprising the biosurfactant of claim 10.

14. A method to improve permeability of formulas, through cell membranes, which are used for cosmetic, pharmaceutical and agrochemical industries comprising including the biosurfactant of claim 10 in the cosmetic, pharmaceutical and agrochemical product thereof.

15. The process according to claim 2, wherein the water is deionized water.

16. The process according to claim 4, wherein the buffered aqueous solution has an osmotic concentration of between 280 and 315 mOsm/L.

17. The process according to claim 9, wherein the temperature is between 10° C. and 25° C.

18. A biosurfactant obtained by the process of claim 1, wherein the biosurfactant has a maximum critical micelle concentration of 420 mg/L, and the elemental composition of the biosurfactant is: between 8.22 and 12.64% of N, between 37.21 and 42.02% of C, between 5.51 and 6.30% of H, wherein the buffered aqueous solution is a saline phosphate buffer.

19. A surfactant and/or emulsifying agent for use in the food, cosmetic, pharmaceutical, agrochemical or environmental industry comprising the biosurfactant of claim 18.

20. A surfactant, emulsifier and/or stabilizer for use in cosmetic, pharmaceutical, and agrochemical purposes comprising the biosurfactant of claim 18.

* * * * *